US00PP14289P29

(12) United States Plant Patent
McDonald

(10) Patent No.: US PP14,289 P2
(45) Date of Patent: Nov. 11, 2003

(54) LEUCANTHEMUM PLANT NAMED 'ANGEL'

(50) Latin Name: *Chrysanthemum leucanthemum*
Varietal Denomination: Angel

(75) Inventor: Daniel Bede McDonald, Seven Hills (AU)

(73) Assignee: University of Sydney, Sydney (AU)

( * ) Notice: Subject to any disclaimer, the term of this patent is extended or adjusted under 35 U.S.C. 154(b) by 0 days.

(21) Appl. No.: 10/223,508

(22) Filed: Aug. 19, 2002

(51) Int. Cl.[7] ..... A01H 5/00
(52) U.S. Cl. ..... Plt./285
(58) Field of Search ..... Plt./285

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Leucanthemum plant named 'Angel', characterized by its upright, compact and uniform plant habit; early flowering habit; anemone-type inflorescences; white-colored ray florets and greenish yellow to white-colored disc florets; and good garden performance.

1 Drawing Sheet

Botanical classification/cultivar designation: *Chrysanthemum leucanthemum* cultivar Angel.

BACKGROUND OF THE INVENTION

The present Invention relates to a new and distinct cultivar of Leucanthemum plant, botanically known as *Chrysanthemum leucanthemum* and hereinafter referred to by the name 'Angel'.

The new Leucanthemum is a product of a planned breeding program conducted by the Inventor in Cobbitty, New South Wales, Australia. The objective of the breeding program is to create compact Leucanthemum cultivars with anemone-type inflorescences.

The new Leucanthemum originated from a cross-pollination made by the Inventor in 1997, in Cobbitty, New South Wales, Australia, of a proprietary selection of *Chrysanthemum leucanthemum* identified as code number Dx97.12.4, not patented, as the female, or seed, parent with a proprietary selection of *Chrysanthemum leucanthemum* identified as code number Dx97.12.8, not patented, as the male, or pollen, parent. The new Leucanthemum was discovered and selected by the Inventor as a single flowering plant within the progeny of the stated cross-pollination grown in a controlled environment in Cobbitty, New South Wales, Australia. The selection of this plant was based on its compact plant habit and anemone inflorescence form.

Asexual reproduction of the new Leucanthemum by vegetative tip cuttings was first conducted in Cobbitty, New South Wales, Australia in 1997. Asexual reproduction by cuttings has shown that the unique features of this new Leucanthemum are stable and reproduced true to type in successive generations.

SUMMARY OF THE INVENTION

The cultivar Angel has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Angel'.

These characteristics in combination distinguish 'Angel' as a new and distinct Leucanthemum:

1. Upright, compact and uniform plant habit.
2. Early flowering habit.
3. Anemone-type inflorescences.
4. White-colored ray florets and greenish yellow to white-colored disc florets.
5. Good garden performance.

Compared to plants of the female parent selection, plants of the new Leucanthemum are more compact and flower earlier. In addition, plants of the female parent selection have single-type inflorescences. Compared to plants of the male parent selection, plants of the new Leucanthemum are more compact. In addition, plants of the male parent selection have single-type inflorescences.

Plants of the new Leucanthemum can be compared to plants of the Leucanthemum cultivar Darling Daisy, not patented. In side-by-side comparisons conducted by the Inventor in Cobbitty, New South Wales, Australia, plants of the new Leucanthemum differed from plants of the cultivar Darling Daisy in the following characteristics:

1. Plants of the new Leucanthemum had longer leaves than plants of the cultivar Darling Daisy.
2. Plants of the new Leucanthemum had larger inflorescences than plants of the cultivar Darling Daisy.
3. Plants of the new Leucanthemum had anemone-type inflorescences whereas plants of the cultivar Darling Daisy had single-type inflorescences.

BRIEF DESCRIPTION OF THE PHOTOGRAPHS

The accompanying colored photographs illustrate the overall appearance of the new Leucanthemum showing the colors as true as it is reasonably possible to obtain in colored reproductions of this type. Colors in the photographs may differ from the color values cited in the detailed botanical description which accurately describe the colors of the new Leucanthemum.

The photograph at the top of the sheet comprises a side perspective view of a typical flowering plant of 'Angel' grown in a container.

The photograph at the bottom of the sheet comprises a close-up view of a typical inflorescence bud, a typical opened inflorescence and the upper and lower surfaces of typical leaves of 'Angel'.

DETAILED BOTANICAL DESCRIPTION

The aforementioned photographs and following observations and measurements describe plants grown in Lompoc, Calif., under commercial practice during the winter and spring in a polycarbonate-covered greenhouse with day temperatures ranging from 18 to 24° C., night temperatures ranging from 16 to 18° C. and light levels ranging from 4,000 to 8,000 foot-candles. Unrooted cuttings were directly planted in 15- cm containers and grown for about 13 weeks.

In the following description, color references are made to The Royal Horticultural Society Colour Chart, 1995 Edition, except where general terms of ordinary dictionary significance are used.

Botanical classification: *Chrysanthemum leucanthemum* cultivar Angel.

Parentage:

*Female, or seed, parent.*—Proprietary selection of *Chrysanthemum leucanthemum* identified as code number Dx97.12.4, not patented.

*Male, or pollen, parent.*—Proprietary selection of *Chrysanthemum leucanthemum* identified as code number Dx97.12.8, not patented.

Propagation:

*Type.*—Vegetative tip cuttings.

*Time to initiate roots.*—About 14 to 18 days.

*Time to produce a rooted young plant.*—About 21 to 28 days.

*Root description.*—Fine, fibrous, white in color.

*Rooting habit.*—Freely branching, dense.

Plant description:

*Appearance.*—Compact, upright and uniform plant habit. Freely basal branching with about 14 or 15 lateral branches per plant; vigorous growth habit.

*Plant height.*—About 17 cm.

*Plant width.*—About 30 cm.

*Lateral branches.*—Length: About 10 cm. Diameter: About 5 mm. Internode length: About 1.5 to 2.5 cm. Strength: Strong. Texture: Pubescent. Color: 144B.

*Foliage description.*—Arrangement: Alternate, simple. Quantity of leaves per lateral stem: About eight. Length: About 12 cm. Width: About 2.2 cm. Shape: Lanceolate to linear. Apex: Acute. Base: Attenuate. Margin: Irregularly dentate. Texture: Upper surface: Pubescent. Lower surface: Glabrous. Venation pattern: Pinnate, arcuate. Color: Young foliage, upper and lower surfaces: 144A. Mature foliage, upper surface: 147A. Mature foliage, lower surface: 147B. Venation, upper surface: 144A. Venation, lower surface: 147C. Petiole: Length: About 6 cm. Diameter: About 6 mm. Texture, upper and lower surfaces: Glabrous. Color, upper and lower surfaces: 144C to 144D.

Inflorescence description:

*Appearance.*—Anemone-type inflorescence form with elongated oblong-shaped ray florets and enlarged disc florets. Inflorescences borne on terminals above foliage. Disk and ray florets develop acropetally on a capitulum. Inflorescences persistent. Inflorescences not fragrant. Typically one terminal inflorescence per lateral branch.

*Flowering response.*—Under natural conditions, plants flower in the spring. Under greenhouse conditions, plant flower year-round. Early flowering, plants begin to flower about ten to eleven weeks after planting unrooted cuttings.

*Inflorescence longevity.*—Inflorescences maintain good color and substance for about two weeks on the plant.

*Inflorescence bud.*—Height: About 1.5 cm. Diameter: About 1.5 cm. Shape: Oblate. Color: 155A.

*Inflorescence size.*—Diameter: About 8.25 cm. Depth (height): About 1.75 cm. Diameter of disc: About 3 cm. Receptacle diameter: About 1.2 cm. Receptacle height: About 5 mm.

*Ray florets.*—Shape: Elongated-oblong, ligulate with longitudinal ridges. Orientation: Initially upright, then about 90° from vertical and with subsequent development, recurved. Length: About 3.5 cm. Width: About 7 mm. Apex: Emarginate. Base: Acute; short corolla tube. Margin: Entire. Texture, upper and lower surfaces: Smooth, glabrous, satiny. Number of ray florets per inflorescence: About 26 arranged in two whorls. Color: When opening, upper surface: 155A. When opening, lower surface: 155B. Fully opened, upper and lower surfaces: More white than 155D.

*Disc florets.*—Arrangement: Massed at center of receptacle. Shape: Tubular, enlarged. Apex: Five-pointed. Length: About 8 mm. Width: At apex, about 4 mm; at base, about 1.5 mm. Number of disc florets per inflorescence: About 250. Color, immature: Apex: 151B. Mid-section and base: 144C. Color, mature: Apex: 155D. Mid-section and base: 144C.

*Phyllaries.*—Quantity/arrangement: About 50 in imbricate whorls. Shape: Elliptic. Apex: Acute. Margin: Entire, membranous. Texture, upper and lower surfaces: Smooth, glabrous. Color: Upper surface: 144B. Lower surface: 144A.

*Peduncles.*—Length: About 10 cm. Diameter: About 3.5 mm. Strength: Strong. Aspect: Mostly erect. Texture: Pubescent. Color: 147B.

*Reproductive organs.*—Androecium: Present on disc florets only. Stamen quantity: Five. Anther shape: Oval. Anther length: About 1.5 mm. Anther color: 14B. Pollen amount: Scarce. Pollen color: 17A. Gynoecium: Present on both ray and disc florets. Pistil quantity: One. Pistil length: About 5 mm. Stigma shape: Bi-lobed. Stigma color: 154C. Style length: About 3 mm. Style color: 150C to 150D. Ovary color: 149D.

*Seed/fruit.*—Seed and fruit production has not been observed.

Disease/pest resistance: Resistance to pathogens and pests common to Leucanthemums has not been observed on plants grown under commercial greenhouse conditions.

Weather tolerance: Plants of the new Leucanthemum have been observed to have good garden performance and have been observed to be tolerant to rain and wind and temperatures from −2 to 35° C.

It is claimed:

1. A new and distinct cultivar of Leucanthemum plant named 'Angel', as illustrated and described.

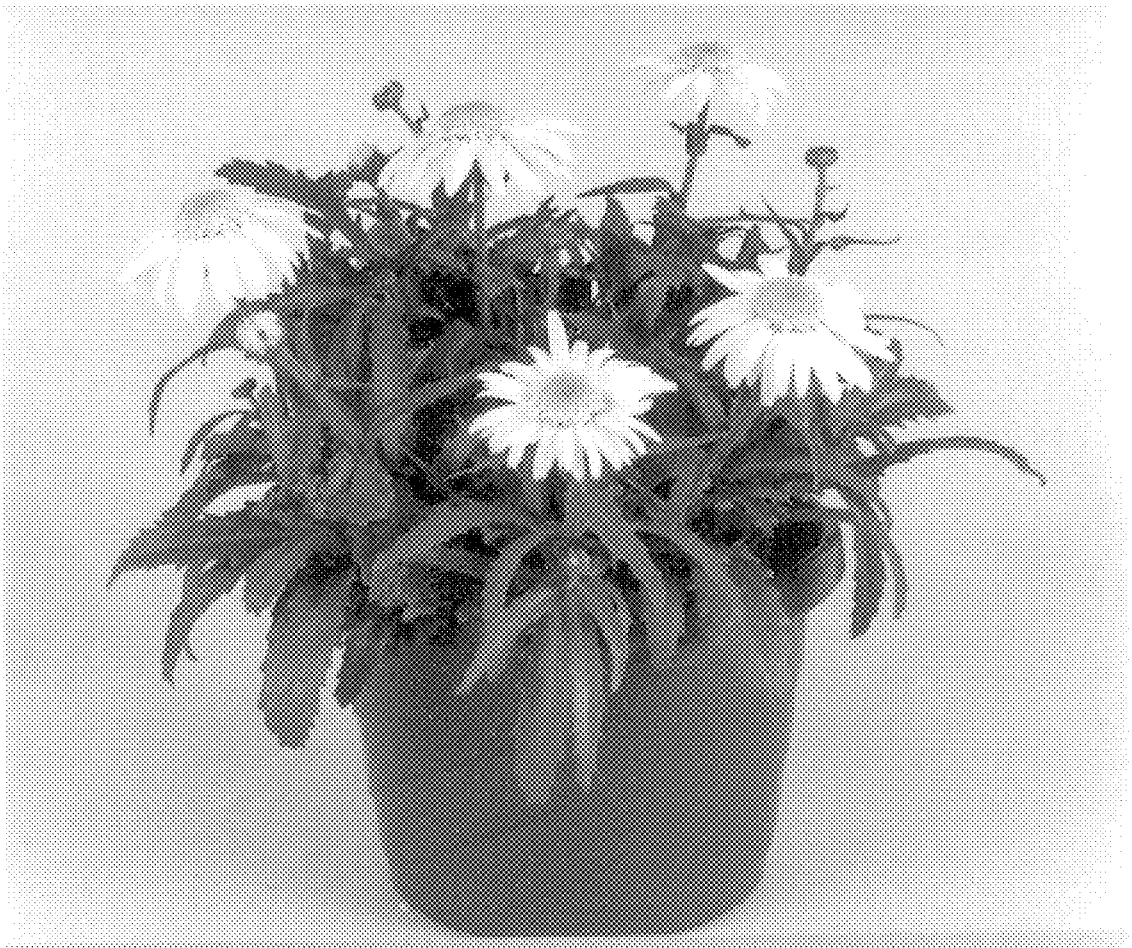
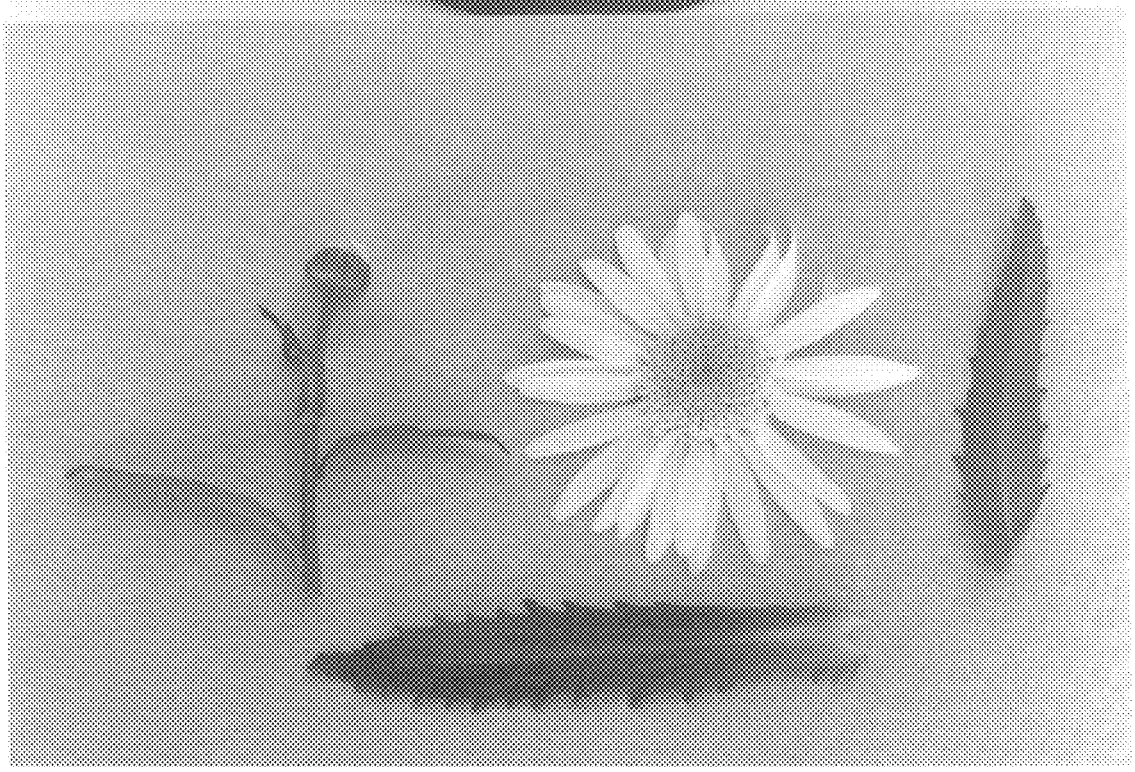

* * * * *